United States Patent [19]
Adams

[11] Patent Number: 4,525,143
[45] Date of Patent: Jun. 25, 1985

[54] ORTHODONTIC DEVICE TO SERVE AS REMOVABLE ANCHORAGE FOR ELASTIC TRACTION BETWEEN UPPER AND LOWER MOLARS

[76] Inventor: Richard M. Adams, 31 McAllister Ave., Kentfield, Calif. 94904

[21] Appl. No.: 592,407

[22] Filed: Mar. 22, 1984

Related U.S. Application Data

[63] Continuation-in-part of Ser. No. 564,231, Dec. 21, 1983, abandoned.

[51] Int. Cl.³ .............................................. A61C 7/00
[52] U.S. Cl. ....................................................... 433/5
[58] Field of Search ...................................... 433/5, 10

[56] References Cited

U.S. PATENT DOCUMENTS 1,938,428  12/1933  Johnson ................................ 433/22
4,245,986   1/1981  Andrews ................................ 433/5

Primary Examiner—Robert Peshock
Attorney, Agent, or Firm—Owen, Wickersham & Erickson

[57] ABSTRACT

An orthodontic device for providing a removable anchorage for elastic traction between upper and lower molars. A smaller-diameter wire having a free posterior end and a larger-diameter wire having a posterior end lying anteriorly to the posterior end of the smaller-diameter wire are connected together well anterior of their posterior ends. At least one wire has stop means thereon spaced from its posterior end, while a short hook depends from at least one wire adjacent to its anterior end. In installation the device is used in conjuction with a first metal band suitable for attachment around an upper molar and having two buccal tubes, namely a larger-diameter tube and a smaller-diameter tube in which are inserted the two wires. A second metal band encircles a lower molar corresponding to the upper molar and has band anchor means on its buccal side. An elastic band joins the anchor means to the hook.

22 Claims, 11 Drawing Figures

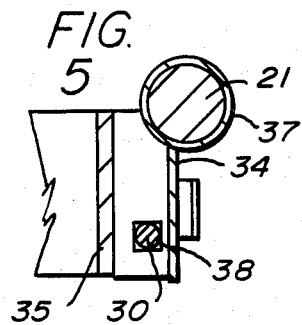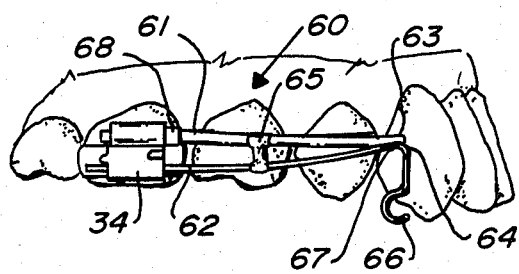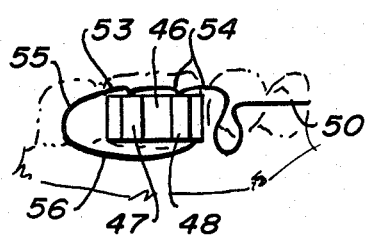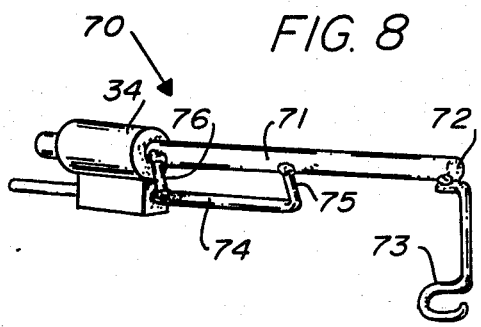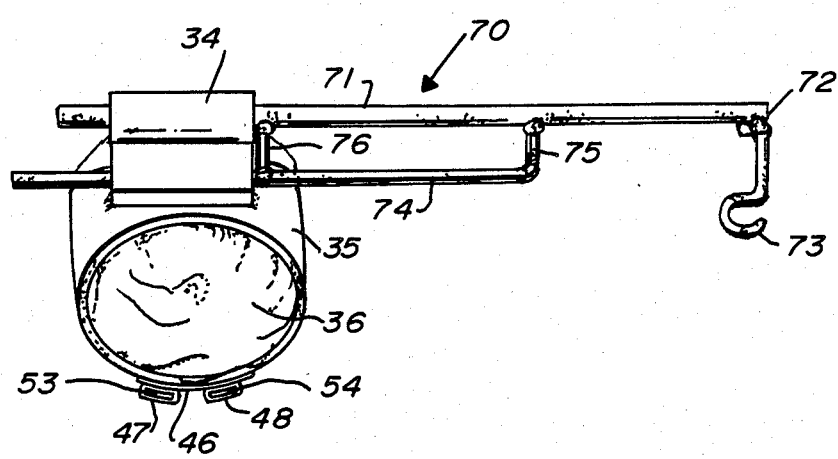

ORTHODONTIC DEVICE TO SERVE AS REMOVABLE ANCHORAGE FOR ELASTIC TRACTION BETWEEN UPPER AND LOWER MOLARS

REFERENCE TO RELATED APPLICATION

This application is a continuation-in-part of application Ser. No. 564,231 filed Dec. 21, 1983 and now abandoned.

This invention relates to an orthodontic device which is readily insertable and removable, to serve as anchorage for elastic traction between upper and lower molars in orthodontic installations affording access to two right or left unused buccal tubes, one rectangular and one round. It also relates to an orthodontic installation including the device.

BACKGROUND OF THE INVENTION

For cosmetic reasons, many children under orthodontic treatment refuse to wear their extra-oral facebow headgear to school and on social occasions. They are usually willing to wear that headgear at home, and even while they are sleeping; however, the reduction in the number of force-minutes each day resulting from not wearing the headgear in public, either prolongs the treatment period or actually causes failure of the treatment.

Heretofore, there has been no adequate part-time substitute for ongoing headgear therapy when the upper or maxillary orthodontic installation consists only of molar band with buccal attachments as anchorage for the facebow-headgear traction device; that is, there has been no device which provided orthodontic treatment and which could be worn to school and other places in public without causing embarrassment to the wearer.

An object of this invention is to provide an intraoral device which can deliver force to the upper and lower molars being treated, thereby eliminating the lost force-minutes, which would otherwise occur during nonuse of the facebow headgear unit.

Another object of the invention is to make it easier to pull forward a lower molar, with or without pulling forward adjacent teeth, while either achieving some rotation of the upper molar, or, with the aid of existing devices, limiting that rotation, or eliminating it.

Another object of the invention is to provide an intraoral device of the type described which can be easily installed and removed by the orthodontic patient.

SUMMARY OF THE INVENTION

The device and installation of this invention are limited in application to instances in which a stable lower molar anchorage is provided or where advancement of the lower dental arch is permissible. If the upper molar needs some rotation, the device can help provide that, and when that rotation is achieved (or if none was needed), a currently available stabilizing unit can be installed to prevent additional or excess upper molar rotation.

The device itself is basically simple. Anchorage to the upper molar is provided by two parallel wires of different diameter and of different length that usually fit respectively into two tubes which are integral parts of or attachments to the buccal surface of a molar band. If there is only one buccal tube, then only one wire can fit within that tube, and the other wire bears against the band itself lying gingival to the tube. The molar bands and the tubes may be any of those presently available commercially. A smaller-diameter wire either bears directly against the band or goes into a small rectangular tube which is provided to receive an arch wire, while the larger-diameter wire goes into a larger-diameter round tube that is provided for the headgear facebow. In instances when an upper archwire is not used in the orthodontic treatment for which this invention is applicable, and since the facebow is necessarily removed during the time when the invention is in use, two tubes are available. Also, when the molar band has three tubes, there may be an upper archwire in place while the invention uses the two tubes not used by the archwire. Even with two tubes, the upper archwire may be left in place, for the smaller-diameter wire can then bear against the band.

To aid in installation, the smaller-diameter wire is made longer at the insertions or anchoring end so that it can be installed into its tube first when there is a tube available for it, and the shorter and larger-diameter wire can then be inserted into its tube. At least one wire is provided with an enlarged portion or stop, so that installation into the tube up to the stop provides exactly the right degree of insertion relative to the tube posteriorly and to the hook anteriorly. If desired, a posterior connector may serve as the stop to limit the insertion of the wires into the tubes, and also as a point of application for force delivered along the parallel wires by the use of an elastic band.

A short hook at the anterior end of the device is soldered to or is part of one wire. The hook engages the elastic band which has been anchored at its other end to a molar band on the lower molar which is opposite to the upper molar band.

The device of this invention does not rely on support from a circumferential arch wire that is inserted into tubes on both right and left molar bands. In fact, if only one molar needs the orthodontic treatment, only one need have the treatment. The device enables continuation of posteriorly directed force on upper molars at times when the facebow headgear is not in use, and yet the device can be easily taken out for installation of the headgear, just as the headgear can easily be taken out for rapid and simple installation of the orthodontic device of this invention.

The installed device is relatively inconspicuous, and is intraoral, so that when installed, it is not likely to embarrass the orthodontic patient, even when he or she is in public.

Other objects and advantages of the invention will appear from the following description of the preferred embodiment.

BRIEF DESCRIPTION OF THE DRAWINGS

FIG. 5 is a view in section taken along the line 5—5 in FIG. 4.

FIG. 6 is a view along the line 6—6 in FIG. 3 looking at the palatal side of the optional stabilizing device installed in place.

FIG. 7 is a view in side elevation of a modified form of orthodontic device of this invention as installed on an upper molar band, showing some of the upper teeth, and before placement of the elastic band.

FIG. 8 is a fragmentary perspective view of an installation like that of FIG. 1 but employing another modified form of the invention.

FIG. 9 is an enlarged bottom view in perspective of the upper molar and its band with the device of FIG. 8 in place.

DESCRIPTION OF SOME PREFERRED EMBODIMENTS

Figure 1:
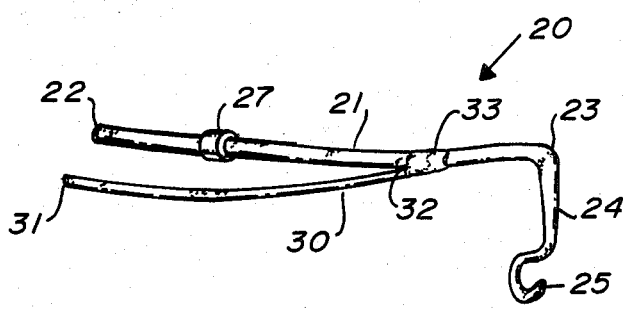
FIG. 1 is a view in perspective of an orthodontic device embodying the principles of the invention.
Figure 2:
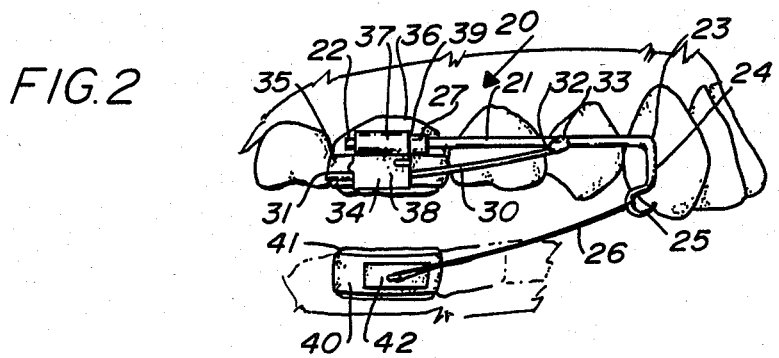
FIG. 2 is a view in elevation of the orthodontic device of FIG. 1 installed in a patient's mouth, with some teeth omitted or shown only in phantom.
Figure 3:
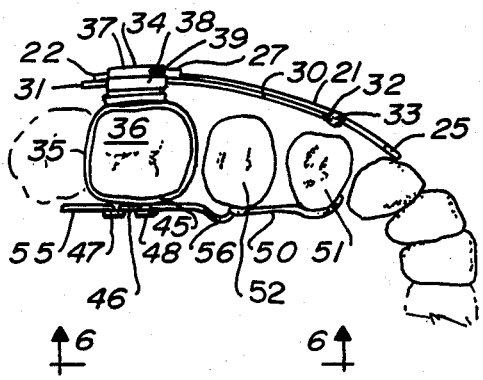
FIG. 3 is a bottom view of the installation of FIG. 2, looking up at the upper teeth, especially at an upper molar, with a stabilizing device also in place.

The orthodontic device 20 shown in FIGS. 1–3 includes a large diameter wire 21, preferably of stainless steel or gold alloy, which may be 0.040 or 0.045 inch in diameter, so as to be 0.006 inch less in diameter than the inner diameter of the larger buccal tube. The wire 21 has a posterior end 22 and an anterior end 23 where a portion 24 is bent down substantially vertically and then bent to form a hook 25 for anchoring an elastic band 26 (see FIG. 2). Spaced away from the posterior end 22 is a stop 27, which is positioned and secured in place by the operator.

The device 20 also has a smaller wire 30, preferably of the same material, 0.020 inch in diameter, which has a posterior end 31 that extends farther posteriorly than the posterior end 22 of the larger wire 21. The posterior portion of the two wires 21 and 30 are approximately parallel, but in the main the wire 30 is angled toward the wire 21. The anterior end 32 of the wire 22 is secured to the larger wire 21 by a suitable solder or brazing joint 33 using the appropriate gold or silver solder. The device 20 curves to correspond to the portion of the dental arch it overlies.

Preferably, the device 20 is manufactured as a standard item but *without* the stop 27 and with the wires 21 and 30 at least as long as the longest likely to be needed. The operator can simply trim off the ends 22 and 31, maintaining the same relative difference in length, so that the smaller wire 30 is the longer one. The stop 27 is placed a distance from the end 23 deemed appropriate by the operator. The stop 27 can be a short sleeve crimped and welded or soldered to the larger diameter wire 21 at the appropriate position by the operator, or may be a mere blob of suitable solder applied by him.

Figure 4:
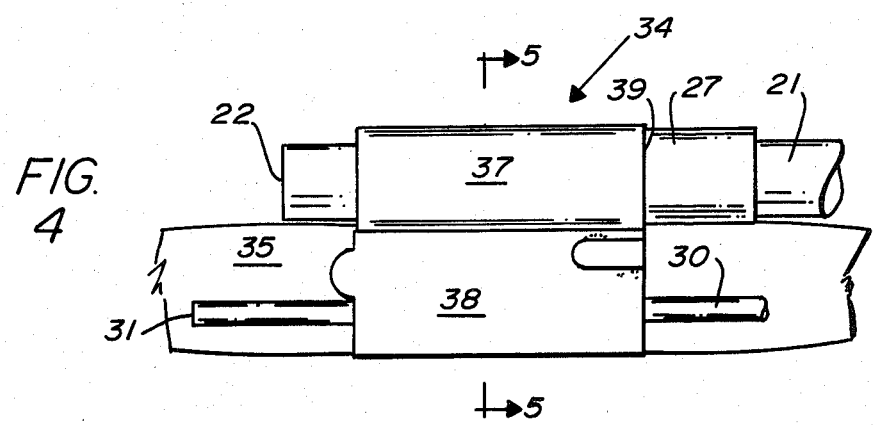
FIG. 4 is an enlarged fragmentary view of the attachment of the device of FIGS. 1-3 to the double buccal tubes.

As shown in FIGS. 2 and 3, the posterior end of the device 20 is inserted into a buccal attachment 34 on a standard type of molar band 35 which has been cemented on an upper molar 36 in the usual manner. The buccal attachment 34 is shown in FIGS. 2 and 3 and is shown in a larger scale in FIGS. 4 and 5. It includes two tubes 37 and 38, the tube 37 being round and of greater diameter than the tube 38, which is rectangular. (In molar bonds having three tubes, only two are used by this invention.) The tube 37 may have an inner diameter of 0.046 inch or 0.051 inch to receive the larger wire 21 and is intended to receive one end of a facebow which, of course, is not in use during the time when the present device 20 is used. However, as stated earlier, it is intended that the device 20 substitute for the facebow when the patient must appear in public. The smaller-diameter tube 38 is rectangular and about 0.022 inch at its shorter width, so that it can receive the smaller wire 30. Heretofore, the tube 38 was used to receive an arch wire, but a postulate of the present invention is that there is no upper arch wire in use because there is in current use a "sliding Class II jig" providing an anterior hook that slides along the circumferential arch wire, providing the same type of traction as described herein. Any type of molar band with buccal attachment can be used, if it has double buccal tubes; so the one illustrated here is shown by way of example only.

Installation of the device 20 after removal of the facebow is quite simple. The patient simply first inserts the posterior end 31 of the smaller wire 30 into the smaller tube 38 and pushes it enough to make sure it is in place. Then the patient aligns the larger wire 21 relative to the larger tube 37, and pushes the wire 21 into the tube 37. Both wires 21 and 30 are pushed on in until the stop 27 abuts the anterior end 39 of the tube 37.

A lower molar band 40 (or similarly effective mechanism) is already in place on a lower molar 41 which is opposite to and corresponds to the upper molar 36. The band 40 has an anchor 42 for an elastic band 26. The user attaches the elastic band 26 to the anchor 42 and slips the other end of the band 26 over the hook 25, and everything is in place.

Removal is, of course, even simpler; it is done simply by taking off the elastic band 26, then sliding out the device 20 from the double buccal tubes; after that, the facebow and its headgear can be installed in the usual manner.

On the palatal or tongue side 45 of the upper molar band 35, there is a bracket 46, preferably having two vertical tubes 47 and 48 for receiving a pair of vertical tubes in a friction fit. From such posts wires extend anteriorly and posteriorly to serve as springs for controlling tooth movement and for locking such a device 50 in place. Preferably, the device 50 is a conventional member normally used to stabilize or move the molar it is attached to (if the device extends to and is anchored by the molar on the opposite side of the dental arch) or to move teeth intermediate to the two molars, or, if used segmentally with the free end resting on the biting surface of a bicuspid 51, to prevent tipping of the molar that is being moved backward by facebow traction, and to guide newly emerging second molars into a favorable position. Here, the device 50 is used instead to prevent rotation of the upper molar 36 by bearing on both bicuspids 51 and 52. The member 50 may be a single wire bent to shape. It forms two vertical posts 53 and 54 that are insertable in the vertical tubes 47 and 48. A somewhat looped portion 55 extending posteriorly from the posts 53 and 54 and an anteriorly extending portion 56 bent to a desired shape to serve as a lock by engaging the gingival portion of the anterior tube 54. The device 50 is inserted to bear on the palatal side of at least one tooth anterior to the molar 36 and, if desired, may be made to bear on the posterior molar also, utilizing the posterior curved portion 55 for the latter purpose.

FIG. 7 shows a modified form of device 60 having a larger-diameter wire 61 and a smaller-diameter wire 62, joined together at their anterior ends 63 and 64 and also by a soldered-on brace 65 which holds their posterior ends generally parallel. A hook member 66 is joined to the anterior ends 63 and 64 by solder 67. A stop 68 is secured by the operator. The posterior ends of the wires are shown properly trimmed.

FIGS. 8 and 9 show another modified form of device 70 which can be made by the operator but is not suitable for commercial pre-manufacture. Here, a larger wire 71 has an anterior end 72 to which a hook member 73 is soldered. A smaller wire 74 is joined to the wire 71 by an anterior cross-member 75 and a posterior cross-member 76 that also serves as the stop. This unit 70 is custom made to the patient, with the wire 74 extending further posteriorly than the wire 71, to enable installation. Otherwise operation is the same.

Figure 10:
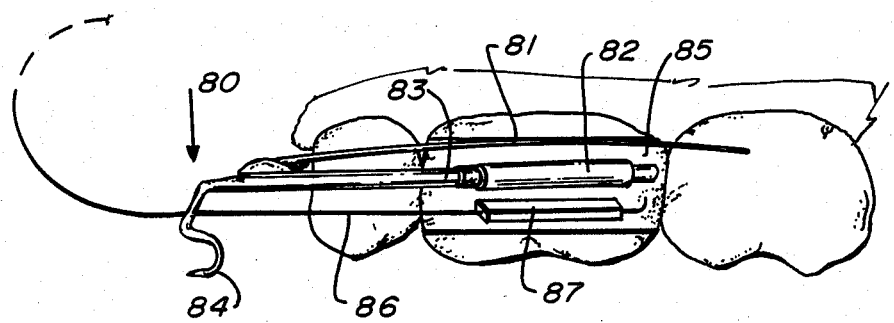
FIG. 10 is a view generally like FIG. 7 of a modified installation and modified device, both embodying the principles of this invention, showing use thereof in connection with an arch wire that is in place.

The orthodontic device of this invention is not limited to use with a double buccal tube nor to use where no archwire is present. FIG. 10 shows an installation of a modified form of device 80 having a smaller-diameter wire 81 lying freely above a large buccal tube 82 into which a larger diameter wire 83 is inserted. In this position buccal rotation of the device's vertical hook 84 is controlled by adjusting the pressure of the small wire 81 palatally against the bracket or band 85. This device is generally preferred for use with a deep bite relationship in which all incisally directed force is contra-indicated in the anterior section of an archwire 86 in the smaller buccal tube 87. The distalizing force of the device 80 is independent of, and has no effect on, the incisors, whereas a vector of force exerted by a sliding jig attached to the small wire 81 is occlusal or incisal.

The device 80 would be preferred over the sliding jig currently in use in the initial stages of 2×4 therapy when very light wire, vulnerable to distortion, is employed.

Figure 11:
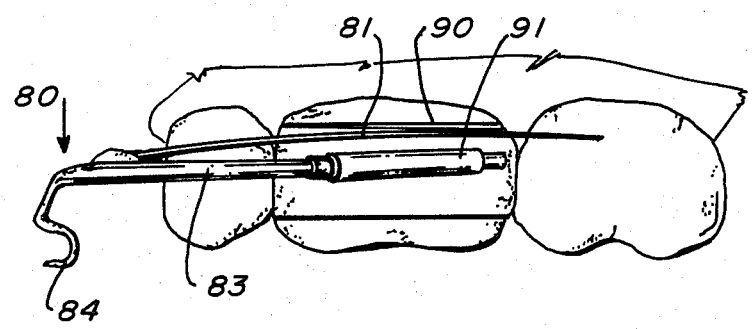
FIG. 11 is a view like FIG. 10 of a different modification in which there is only one buccal tube on the band and no archwire.

FIG. 11 shows the instance in which a band 90 having only one buccal tube 91 is used, with the larger-diameter wire 83 inserted in it. Again, the smaller-diameter wire bears against the band 90.

To those skilled in the art to which this invention relates, many changes in construction and widely differing embodiments and applications of the invention will suggest themselves without departing from the spirit and scope of the invention. The disclosures and the descriptions herein are purely illustrative and are not intended to be in any sense limiting.

What is claimed is:

1. An orthodontic installation providing a removable anchorage for elastic traction between upper and lower molars, comprising:
   a first metal band for attachment around an upper molar, said band having at least one buccal tube,
   an assembly comprising a smaller-diameter wire having a posterior end engaging said band, a larger-diameter wire having a posterior end entering said buccal tube from the anterior side of said first band, connecting means connecting said wires together anteriorly of their posterior end, stop means on said assembly to engage a said tube, to limit the length of entry into said tube, and a short hook extending down from the anterior end of said larger-diameter wire,
   a second metal band encircling a lower molar corresponding to said upper molar, and having anchor means on its buccal side, and
   an elastic band joining said lower molar anchor means to said upper hook.

2. The orthodontic installation of claim 1 wherein:
   a said first metal band has a palatal bracket, and
   tooth stabilizing means attached to said palatal bracket and bearing on at least one upper tooth anterior to said upper molar.

3. The orthodontic installation of claim 2 wherein said palatal bracket has two vertical tubes and said tooth stabilizing means has two posts fitting in said tubes.

4. The orthodontic installation of claim 1 wherein the smaller-diameter wire extends posteriorly further than the larger-diameter wire.

5. The orthodontic installation of claim 1 wherein said larger-diameter wire and said hook are integral.

6. The orthodontic installation of claim 5 wherein said hook is a narrower extension of said larger-diameter wire and is oriented vertically beneath the end of said wire.

7. The orthodontic installation of claim 1 wherein said hook is soldered to the anterior end of said larger-diameter wire.

8. The orthodontic installation of claim 7 wherein said smaller-diameter wire is secured to said larger-diameter wire and to said hook by the same solder attachment attaching said hook to said larger-diameter wire.

9. The orthodontic installation of claim 1 wherein said smaller-diameter wire joins said larger-diameter wire and is soldered to it in between said stop and the anterior end of said larger-diameter wire.

10. The orthodontic installation of claim 1 wherein said larger-diameter and smaller-diameter wires are parallel, except for a finial anterior of said smaller-diameter wire that is turned at substantially a right angle and the end of which is soldered to said larger-diameter wire at a spaced distance from said stop.

11. The orthodontic installation of claim 10 wherein said stop is provided by a member generally perpendicular to and bridging said larger-diameter and smaller-diameter wires, being soldered to both of them at its extremities.

12. An orthodontic installation providing a removable anchorage for elastic traction between upper and lower molars, comprising:
   a first metal band for attachment around an upper molar, said band having at least two buccal tubes, namely a larger-diameter tube and a smaller-diameter tube,
   an assembly comprising a smaller-diameter wire having a posterior end entering said smaller-diameter tube, a larger-diameter wire having a posterior end entering said larger-diameter tube, both entering from the anterior side of said first band, connecting means connecting said wires together anteriorly of their posterior end, at least one said wire having stop means thereon to engage its associated said tube, to limit the length of entry of both wires into their said tube, and a short hook extending down from the anterior end of said larger-diameter wire,
   a second metal band encircling a lower molar corresponding to said upper molar, and having anchor means on its buccal side, and
   an elastic band joining said lower molar anchor means to said upper hook.

13. The orthodontic installation of claim 1 wherein the smaller-diameter wire extends posteriorly further than the larger-diameter wire.

14. The orthodontic installation of claim 13 wherein the larger-diameter buccal tube is round in cross-section and the smaller-diameter buccal tube is rectangular in cross-section and both said wires are round in cross-section.

15. An orthodontic installation providing a removable anchorage for elastic traction between upper and lower molars, comprising:
   a first metal band for attachment around an upper molar, said band having at least one buccal tube,
   an assembly comprising a smaller-diameter wire having a posterior end engaging the outer surface of said first band, a larger-diameter wire having a posterior end entering said buccal tube, entering from the anterior side of said first band, connecting means connecting said wires together anteriorly of their posterior end, said larger-diameter wire having stop means thereon to engage said buccal tube, to limit its length of entry into said tube, and a short hook extending down from the anterior end of said larger-diameter wire,
   a second metal band encircling a lower molar corresponding to said upper molar, and having anchor means on its buccal side, and
   an elastic band joining said lower molar anchor means to said upper hook.

16. An orthodontic device for providing a removable anchorage for elastic traction between upper and lower molars comprising:
   a smaller-diameter wire having a free posterior end,
   a larger-diameter wire having a posterior end lying anteriorly to the posterior end of said smaller-diameter wire, at least one said wire having stop means thereon spaced from its said posterior end,
   connecting means rigidly connecting said wires together well anterior of their posterior ends, and
   a short hook secured to at least one said wire adjacent to its anterior end.

17. The orthodontic device of claim 16 wherein the smaller-diameter wire extends posteriorly further than the larger-diameter wire.

18. The orthodontic device of claim 16 wherein said larger-diameter wire and said hook are integral.

19. The orthodontic device of claim 16 wherein said hook is soldered to the anterior end of said larger-diameter wire.

20. The orthodontic device of claim 16 wherein said smaller-diameter wire is secured to said larger-diameter and to said hook by the same solder attachment attaching said hook to said larger-diameter wire.

21. The orthodontic device of claim 16 wherein said smaller-diameter wire joins said larger-diameter wire and is soldered to it in between said stop and the anterior end of said larger-diameter wire.

22. The orthodontic device of claim 16 wherein said larger-diameter and smaller-diameter wires are parallel, except for a finial anterior of said smaller-diameter wire that is turned at substantially a right angle and the end of which is soldered to said larger-diameter wire at a spaced distance from said stop.

* * * * *